(12) United States Patent
Geist et al.

(10) Patent No.: US 12,016,703 B2
(45) Date of Patent: *Jun. 25, 2024

(54) ESOPHAGEAL MONITORING

(71) Applicant: CIRCA Scientific, Inc., Englewood, CO (US)

(72) Inventors: Leroy D. Geist, Parker, CO (US); LeRoy D. Jutte, Highlands Ranch, CO (US)

(73) Assignee: CIRCA Scientific, Inc., Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/203,595

(22) Filed: May 30, 2023

(65) Prior Publication Data

US 2023/0380767 A1    Nov. 30, 2023

Related U.S. Application Data

(63) Continuation of application No. 17/348,679, filed on Jun. 15, 2021, now Pat. No. 11,660,051, which is a
(Continued)

(51) Int. Cl.
*A61B 5/00* (2006.01)
*A61B 5/01* (2006.01)
(Continued)

(52) U.S. Cl.
CPC ............. *A61B 5/687* (2013.01); *A61B 5/0084* (2013.01); *A61B 5/01* (2013.01); *A61B 5/065* (2013.01); *A61B 5/4233* (2013.01); *A61B 5/4836* (2013.01); *A61B 90/36* (2016.02); *A61B 90/37* (2016.02); *A61B 5/0538* (2013.01); *A61B 2017/00088* (2013.01); *A61B 2034/2051* (2016.02); *A61B 2090/309* (2016.02); *A61B 90/361* (2016.02); *A61B 2090/372* (2016.02); *A61B 2505/05* (2013.01);
(Continued)

(58) Field of Classification Search
CPC ......... A61B 5/687; A61B 5/0084; A61B 5/01; A61B 5/065; A61B 5/4233; A61B 5/4836; A61B 90/36; A61B 90/37; A61B 5/0538; A61B 90/361; A61B 2017/00088; A61B 2034/2051; A61B 2090/309; A61B 2090/372; A61B 2505/05; A61B 2562/0247; A61B 2562/043; A61B 2562/166; A61B 1/2733; A61B 5/6859
See application file for complete search history.

*Primary Examiner* — Jonathan T Kuo
(74) *Attorney, Agent, or Firm* — DENTONS Durham Jones Pinegar (57) ABSTRACT

An esophageal monitoring device includes a camera and, optionally, one or more lights to enable visualization of an interior of a subject's esophagus. Visualization of the interior of the subject's esophagus before and after a left atrial ablation procedure may enable a healthcare provider to determine whether or not the left atrial ablation procedure has damaged the subject's esophagus before the subject experiences any symptoms of such damage. An esophageal monitoring device may also include sensors and/or markers that enable a determination of its location within a subject's esophagus. Such an esophageal monitoring device may be configured for three-dimensional mapping, and enable the generation of an accurate three-dimensional map of the physical relationship between a subject's esophagus and the left atrium of his or her heart. Methods of monitoring a subject's esophagus while a left atrial ablation procedure is being conducted on the subject's hear are also disclosed.

20 Claims, 6 Drawing Sheets

Related U.S. Application Data continuation of application No. 15/625,929, filed on Jun. 16, 2017, now Pat. No. 11,033,232.

(60) Provisional application No. 62/350,833, filed on Jun. 16, 2016.

(51) Int. Cl.
*A61B 5/0538* (2021.01)
*A61B 5/06* (2006.01)
*A61B 17/00* (2006.01)
*A61B 34/20* (2016.01)
*A61B 90/00* (2016.01)
*A61B 90/30* (2016.01)

(52) U.S. Cl.
CPC . *A61B 2562/0247* (2013.01); *A61B 2562/043* (2013.01); *A61B 2562/166* (2013.01)

ESOPHAGEAL MONITORING

CROSS-REFERENCE TO RELATED APPLICATION

This application is a continuation of U.S. patent application Ser. No. 17/348,679, filed Jun. 15, 2021 and titled ESOPHAGEAL MONITORING ("the '679 application"), now U.S. Pat. No. 11,660,051, issued May 30, 2023, which is a continuation of U.S. patent application Ser. No. 15/625,929, filed Jun. 16, 2017 and titled ESOPHAGEAL MONITORING ("the '929 application"), now U.S. Pat. No. 11,033,232, issued Jun. 15, 2021, which claims the benefit of priority to the Jun. 16, 2016 filing date of U.S. Provisional Patent Application No. 62/350,833, titled ESOPHAGEAL MONITORING ("the '833 Provisional Application") is hereby made pursuant to 35 U.S.C. § 119(e). The entire disclosures of the '679 application, the '929 Application, and the '833 Provisional Application are hereby incorporated herein.

TECHNICAL FIELD

This disclosure relates to esophageal monitoring, as may be conducted while conducting an ablation procedure on the left atrium of a subject's heart. More specifically, this disclosure relates to esophageal monitoring methods that occur in conjunction with visualization of the esophagus. Even more specifically, a subject's esophagus may be visualized before and after an ablation procedure has been conducted on the left atrium of the subject's heart. In addition, this disclosure relates to esophageal monitoring systems and to esophageal monitoring devices.

RELATED ART

A variety of techniques have been developed in which tissues or organs in a patient's body are heated or cooled. Tissues may be heated by a variety of techniques, including high frequency ultrasound, radiofrequency (RF) treatments, laser treatments, use of infrared radiation, and by direct application of thermal energy. Cooling is often effected cryogenically. Techniques that heat and cool tissues may be collectively referred to as "thermal techniques."

Thermal techniques are useful for treating a variety of disease states. The degree of heating or cooling that is required to optimize the efficiency of some thermal techniques may adversely affect tissues or organs that are adjacent to a treated tissue or organ. For example, a great deal of heat is generated by radiofrequency (RF) waves when electrophysiological ablation techniques are used to remove faulty electrical pathways from the hearts H of human subjects who are prone to developing cardiac arrhythmias, such as fibrillation in the left atria LA of their hearts H. In addition to heating and treating the diseased tissue in the heart H, the esophagus E, which is located close to the left atrium LA of the heart H, as shown in FIG. 1, may also be heated.

Figures 1, 2:
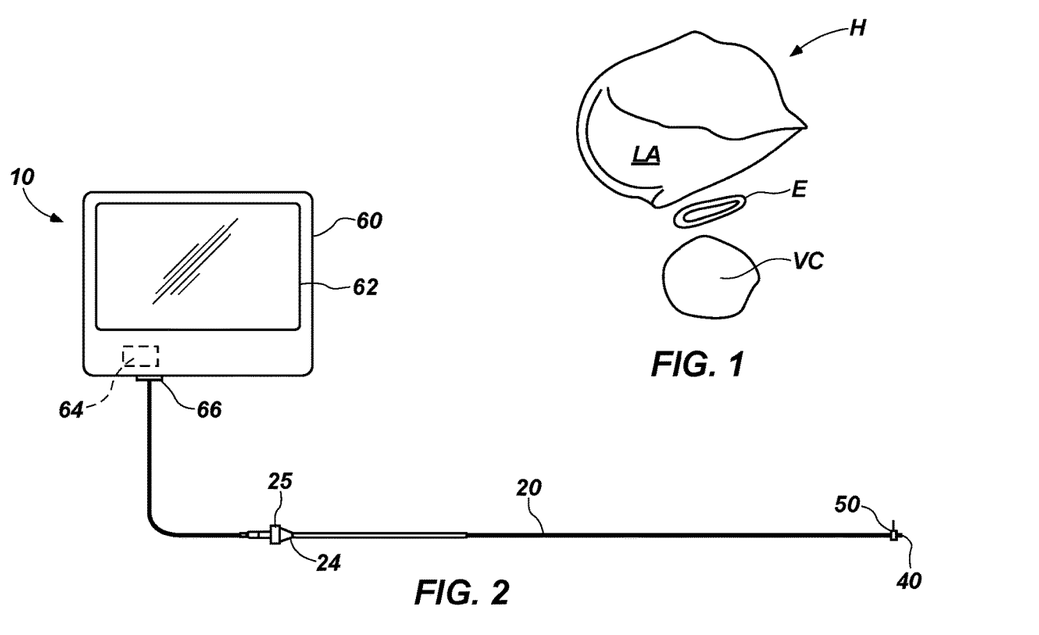
FIG. 1 is a diagram depicting the arrangement of the left atrium of the heart and the esophagus of a subject.
FIGS. 2 and 3 depict an embodiment of an esophageal monitoring system according to this disclosure.

As FIG. 1 illustrates, a typical human esophagus E typically has a narrow, or flat, oval cross-sectional shape, taken along a length of the esophagus E, that resembles a pancake, with a large portion of the outer surface of the esophagus E located between the posterior wall of the left atrium LA (i.e., the location where ablation procedures are typically conducted in the left atrium LA) and the vertebral column VC, although the size, shape, and/or position of the esophagus E may vary. In an average human adult, about 70 mm of the length and the majority of the front side of a 18 mm width of esophagus E is located in proximity to or contacts the posterior wall of the left atrium LA. As a consequence of the intimate arrangement between the esophagus E and the left atrium LA, the heat generated during ablation of the left atrium LA may damage the esophagus E and may, in some cases, create an esophageal fistula. Unfortunately, the complications that arise from esophageal fistula may not present themselves until weeks after the left atrial ablation procedure and, in many cases, at too late a time to treat and/or cure the sometimes fatal damage that has been done.

In recognition of the potentially dire consequences of overheating the esophagus E during ablation of the left atrium LA, physicians have started using devices that monitor temperature within a subject's esophagus E during left atrial ablation procedures. If the sensed temperature reaches a predetermined level, the physician may momentarily discontinue the left atrial ablation procedure to allow the esophagus E to cool and, hopefully, to prevent any damage to the esophagus E.

The use of temperature probes has been shown to reduce or eliminate the damage, including the formation of one or more fistulas, that could otherwise be incurred by the esophagus E as ablation procedures are being performed on the posterior wall of the left atrium LA of the heart H. Nevertheless, healthcare providers typically do not receive any feedback regarding the usefulness of temperature probes unless complications arise from damage caused to the esophagus E by the left atrial ablation procedure. Again, that damage may not present itself for days or weeks and, by the time it does present itself, it may not be correctable.

SUMMARY

A method for monitoring an esophagus of a subject, or "esophageal monitoring," during ablation of the left atrium of the subject's heart includes visualizing the esophagus after the left atrial ablation procedure, while removing an esophageal monitoring device from the subject's esophagus. In some embodiments, the esophagus may also be visualized while inserting the esophageal monitoring device into the esophagus.

A method for esophageal monitoring according to this disclosure may be performed as part of a procedure for ablating faulty electrical pathways in the posterior wall of the left atrium; i.e., left atrial ablation. In such a method, an esophageal monitoring device may be introduced into a subject's esophagus prior to ablation of the posterior wall of the left atrium. In some embodiments, the esophagus and its condition prior to the left atrial ablation procedure may be visualized and optionally recorded as the esophageal monitoring device is introduced into the esophagus. With the esophageal monitoring device in place against an inner surface of a portion of the esophagus that is located in proximity to the posterior wall of the left atrium, the posterior wall of the left atrium may be ablated. During left atrial ablation procedure, the esophageal monitoring device is used to monitor the inner surface of the portion of the esophagus against which the esophageal monitoring device has been placed. Once the left atrial ablation procedure is compete, the esophageal monitoring device may be removed from the esophagus. As the esophageal monitoring device is removed from the esophagus, the esophagus and its condition following the left atrial ablation procedure may be visualized and optionally recorded. As used herein, the term "visualize" includes obtaining images (e.g., still images, video images, etc.) of the inner surface of the esophagus and making the images available to a healthcare provider for viewing. Viewing of the images may occur contemporaneously with introduction of the esophageal monitoring device into the esophagus and/or with removal of the esophageal monitoring device from the esophagus. Alternatively, the images may be viewed at a later time (e.g., after completion of the left atrial ablation procedure, etc.).

Visualization of the esophagus during insertion of the esophageal monitoring device or during removal of the esophageal monitoring device may be accompanied by position reference monitoring, in which the position of the esophageal monitoring device relative to the esophagus (e.g., a depth the esophageal monitoring device has been inserted into the esophagus, etc.) is periodically determined. Position reference monitoring may include sensing position reference features on an insertion component (e.g., a catheter, another tube, etc.) for the esophageal monitoring device or on the esophageal monitoring device as the position reference features pass one or more fixed locations. More specifically, position reference monitoring may occur as position reference features move past one or more position sensors, which may be located at substantially fixed locations relative to the subject's esophagus (e.g., at a location outside the subject's body in embodiments where the position reference features are carried by the insertion component or the esophageal monitoring device, along a length of an insertion component in embodiments where the position reference features are carried by the esophageal monitoring device, etc.). The position reference features may be spaced at various intervals (e.g., 5 mm, 1 cm, etc.) along a length of the insertion component or the esophageal monitoring device (e.g., a proximal element of the esophageal monitoring device, etc.). In embodiments where visualization of the inner surface of the esophagus includes capturing still images of the esophagus, as each position reference feature passes the position sensor, the position sensor or the position reference feature may cause a camera carried by the esophageal monitoring device to capture a still image, synchronizing each image with the depth, or location, of the esophageal monitoring device in the esophagus. In embodiments where visualization of the inner surface of the esophagus comprises capturing video images, the position sensor or the position reference feature may cause a mark (e.g., a depth interval mark, a depth mark, etc.) to be placed on the video image to synchronize the depth, or location, of the esophageal monitoring device in the esophagus with the images shown in the video. In any event, position reference monitoring may enable correlation of the images of the inner surface of the esophagus to their relative positions along the length of the esophagus.

In embodiments where visualization of the esophagus occurs while introducing the esophageal monitoring device into the esophagus, the images obtained by such visualization may provide a baseline, or reference, for subsequent comparison. Thus, by comparing the images obtained after the ablation procedure, which may be referred to as "after images," to the images obtained before the ablation procedure, which may be referred to as "before images," a healthcare provider (e.g., a physician, a physician's assistant, etc.) can identify any new trauma to the inner surface of the esophagus during the left atrial ablation procedure, while introducing the esophageal monitoring device into the esophagus, or while removing the esophageal monitoring device from the esophagus. In some embodiments, light may be used to facilitate visualization of the inner surface of the esophagus. So-called "white light" (i.e., a combination of various colors of visible light) may be used to illuminate the dark spaces and surfaces within the esophagus. Various wavelengths of electromagnetic radiation (e.g., ultraviolet radiation, infrared radiation, etc.) may be used to reveal trauma or evidence of trauma (e.g., increased blood flow to a particular location, etc.) before it would otherwise be visible when illuminated with white light.

The monitoring that occurs during the left atrial ablation procedure may provide some indication of the danger of the ablation procedure to the esophagus. In some embodiments, temperature may be monitored across the inner surface of the portion of the esophagus located adjacent to the posterior wall of the left atrium. Temperature monitoring may occur at a plurality of locations (e.g., arranged in an area array, etc.) across the area of the inner surface of the portion of the esophagus located adjacent to the posterior wall of the left atrium. Such temperature monitoring may occur in real-time throughout the left atrial ablation procedure (e.g., frequently, continuously, etc.). By monitoring the temperature of the esophagus, a healthcare provider may be able to readily determine whether or not the left atrial ablation procedure is heating the esophagus to a potentially damaging temperature and, thus, inform the healthcare provider when one or more affirmative actions (e.g., temporary termination of ablation, reducing the force of the ablation catheter against the interior surface of the left atrium, movement of the esophagus away from the left atrium, etc.) should be taken to prevent damage to the esophagus.

In the event that visualization of the inner surface of the esophagus after a left atrial ablation procedure has been performed on the posterior wall of the left atrium of a subject's heart reveals that the esophagus has been traumatized or damaged, a healthcare professional may diagnose and treat the damage. Such treatment may be provided immediately following the left atrial ablation procedure or shortly after the left atrial ablation procedure (e.g., within one day of the left atrial ablation procedure, within two days of the left atrial ablation procedure, etc.). In some cases, visualization of the interior surfaces of the esophagus in connection with a left atrial ablation procedure may enable healthcare professionals to treat damage to the esophagus before the subject experiences any adverse symptoms from the left atrial ablation procedure.

Another embodiment of monitoring may include monitoring pressure or force across the inner surface of the portion of the esophagus located adjacent to the posterior wall of the left atrium. More specifically, the force of the esophageal monitoring device against the wall of the esophagus may be monitored and/or the force of the esophagus against the esophageal monitoring device may be monitored. Even more specifically, the amount of pressure applied against the esophageal monitoring device by the inner surface of the relevant portion of the esophagus (i.e., the portion of the esophagus in proximity to the left atrium of the heart) may be monitored. Pressure monitoring may occur at a plurality of locations (e.g., arranged in an area array, etc.) across the area of the inner surface of the portion of the esophagus located adjacent to the posterior wall of the left atrium. Such pressure monitoring may occur in real-time, frequently throughout the ablation procedure or continuously throughout the left atrial ablation procedure. Pressure monitoring may also occur before and/or after the ablation procedure). Monitoring the pressure or the force applied by the esophageal wall to the esophageal monitoring device may be used to provide an indication of the potential or actual effects that the application of force by the ablation catheter to the interior surface of the left atrium and/or of the application of force by the esophageal monitoring device against the esophageal wall on the proximity of the esophagus to the left atrium, on the pressure or force between the left atrium and the esophagus (although such pressure or force is indirect as it is applied directly against the pericardium) and, thus, on the potential for damage to the esophagus during the left atrial ablation procedure. As a specific, but non-limiting example, monitoring the pressure or force applied to the esophageal monitoring device by the inner surface of the portion of the esophagus located adjacent to the posterior wall of the left atrium may indicate whether or not the individual performing the left atrial ablation procedure is forcing the posterior wall of the left atrium toward the outer surface of the esophagus and, thus, increasing the likelihood that potentially damaging temperatures (e.g., heat or cold) would be transmitted from the left atrium to the esophagus.

A system for monitoring a condition of a subject's esophagus while an ablation procedure is being performed on the posterior wall of the left atrium of the subject's heart includes an esophageal monitoring device capable of providing images of an inner surface of the esophagus. More specifically, the esophageal monitoring device may include a proximal element, a monitoring element at a distal end of the proximal element, and a camera (e.g., a CMOS (complementary metal-oxide semiconductor) imager, a CCD (charge-coupled device camera), etc.). Optionally, the esophageal monitoring device may include an insertion component that facilitates insertion of the monitoring element into the esophagus, and that may facilitate withdrawal of the monitoring element from the esophagus.

The proximal element of the esophageal monitoring device may comprise an elongated element. The proximal element may carry various features (e.g., proximally located electrical connectors, wires, electrical traces, etc.) that enable the communication of signals between corresponding features at or near a distal end of the esophageal monitoring device (e.g., temperature sensors and/or pressure sensors or force sensors of the monitoring element, the camera, one or more lights (LEDs (light-emitting diodes), etc.), etc., within the subject's esophagus) and equipment connected to a proximal end of the proximal element (e.g., monitors and other devices outside of the subject's body). These features may be carried by (e.g., laminated onto, integrally formed with, etc.) a substrate of the proximal element.

The monitoring element of the esophageal monitoring device may be located at a distal end of the proximal element. In various embodiments, the monitoring element may have a width or may be capable of assuming an expanded width; i.e., a width that exceeds a width of the proximal element. In some embodiments, the expanded width of the monitoring element may effectively impart the monitoring element with an area that is about the same as or larger than the area of a portion of the esophagus located adjacent to the posterior wall of the left atrium of the heart (e.g., at least about 58 mm by at least about 14 mm, or at least about 812 mm$^2$; about 60 mm by about 15 mm, or about 900 mm$^2$; about 70 mm by about 18 mm, or about 1,260 mm$^2$; about 100 mm by about 20 mm, or about 2,000 mm$^2$; etc.). Sensors may be positioned across an area occupied by the monitoring element. The sensors may include temperature sensors, pressure sensors and/or force sensors, or a combination thereof. In some embodiments, positional markers of the type used in anatomic mapping (e.g., impedance electrodes used in impedance-based anatomical mapping, etc.) may also be positioned across an area occupied by the monitoring element.

In a specific embodiment, the monitoring element may include a plurality of branches that may be oriented somewhat parallel to one another, substantially parallel to one another, or parallel to each other. Even more specifically, the monitoring element may include three branches, with a center branch being collinear with, or even an extension of, the proximal element of the esophageal monitoring device. The branches diverge from the proximal element of the esophageal monitoring device at a proximal end of the monitoring element; the separate free ends of the branches are located at a distal end of the monitoring element.

The branches of the monitoring element may be capable of being folded, one atop another. For example, the branches may be folded upon one another into a retracted arrangement while the monitoring element resides within the lumen of the insertion component, but unfold as the monitoring element is deployed, or extends, distally beyond the distal end of the insertion component. Conversely, the distal end of the insertion component and a proximal end of the monitoring element may be mutually configured to enable the branches of the monitoring element to fold upon one another as the esophageal monitoring device is pulled proximally and the monitoring element is pulled proximally back into the insertion component.

When the monitoring element is in an expanded (e.g., deployed, unfolded, etc.) configuration, it may occupy an area that is about the same as or larger than the area of a portion of the esophagus located adjacent to the posterior wall of the left atrium of the heart (e.g., at least about 58 mm by at least about 14 mm, or at least about 812 mm$^2$; at least about 70 mm by at least about 18 mm, or at least about 1,260 mm$^2$; etc.). In a specific embodiment, the area occupied by the expanded monitoring element may be about 60 mm by about 15 mm, or about 900 mm$^2$. In another specific embodiment, the area occupied by the expanded monitoring element may be about 70 mm by about 18 mm, or about 1,260 mm$^2$. In yet another specific embodiment, the area occupied by the expanded monitoring element may be about 100 mm by about 20 mm, or about 2,000 mm$^2$.

The area occupied by the branches of the monitoring element may be substantially two-dimensional. Alternatively, the branches of the monitoring element may be arranged to occupy a three-dimensional space. For example, the branches of the monitoring element may be bent or curved and arranged in a manner that enables them to be placed against an interior surface of a subject's esophagus without requiring that a remainder of the esophageal monitoring device or the insertion component be forced against an internal surface of the esophagus. As another example, the branches of the monitoring element may be arranged in a manner that approximates a shape or curvature of the interior surface of the esophagus against which they are to be placed.

Each branch of the monitoring element carries a plurality of sensors (e.g., temperature sensors, pressure sensors or force sensors, etc.). Optionally, each branch of the monitoring element may also carry one or more positional markers (e.g., impedance electrodes used in impedance-based anatomical mapping, etc., which may be used to three-dimensionally map the location of the monitoring element within the esophagus and relative to the left atrium of the subject's heart and, when used in conjunction with measurements of the pressure or force exerted on pressure sensors or force sensors of the monitoring element, may be used to map the physical relationship between the left atrium and the esophagus, as well as any changes to that physical relationship (e.g., force of the left atrium against the pericardium, which is then transmitted to the esophagus, etc.)). When the branches are positioned laterally adjacent to one another, the sensors and positional markers, if any, may be positioned across an area occupied by the branches of the monitoring element. With the monitoring element in an expanded configuration, the sensors and positional markers, if any, carried by its branches may be spread over the area occupied by the monitoring element. In some embodiments, the sensors and markers, if any, may be arranged in one or more arrays across the area occupied by the monitoring element. The monitoring element of the esophageal monitoring device may also carry a camera, one or more lights, etc., as described previously herein.

In embodiments of the esophageal monitoring device that include an insertion component, the insertion component may comprise a tube, a catheter, or a similar structure. At least a portion of the esophageal monitoring device may be disposed within the insertion component (e.g., a lumen thereof, a channel thereof, etc.) as that portion of the esophageal monitoring device is introduced into a subject's esophagus. In addition, the insertion component may be configured to enable the esophageal monitoring device to be pushed distally therethrough, enabling a distal portion of the esophageal monitoring device, such as the monitoring element thereof, to be deployed from the distal end of the insertion component. In embodiments where the monitoring element includes three branches, the side branches may be folded over the center branch and over each other.

The proximal element and the monitoring element of the esophageal monitoring device may have any suitable construction. In a specific embodiment, the proximal element and the monitoring element of the esophageal monitoring device may comprise a flexible printed circuit board, or "flex PCB" or "flex circuit" that carries conductive traces, or "wires," contacts, sensors, and other optional components (e.g., a camera, one or more lights, positional markers, etc.).

A system for monitoring a condition of a subject's esophagus during a left atrial ablation procedure may also include an insertion component, such as a catheter or another tube, with a lumen within which at least a portion of the esophageal monitoring device may be disposed as that portion of the esophageal monitoring device is introduced into a subject's esophagus. The insertion component may be configured to enable a distal portion of the esophageal monitoring device, such as the camera, to protrude therefrom. In addition, the insertion component may be configured to enable the esophageal monitoring device to be pushed distally therethrough, enabling a distal portion of the esophageal monitoring device, such as the monitoring element thereof, to be deployed distally from the distal end of the insertion component.

In embodiments where the monitoring element includes branches, the branches may be folded upon one another while the monitoring element resides within the lumen of the insertion component, but unfold as the monitoring element is deployed, or extends, distally beyond the distal end of the insertion component. Conversely, the distal end of the insertion component and a proximal end of the monitoring element may be mutually configured to enable the branches of the monitoring element to fold upon one another as the esophageal monitoring device is pulled proximally and the monitoring element is pulled proximally back into the insertion component.

In some embodiments, the camera of the system may be positioned at or adjacent to a distal end of the esophageal monitoring device. More specifically, the camera of the system may be positioned at or adjacent to a distal end of the monitoring element of the esophageal monitoring system. In embodiments where the monitoring element is branched, the camera may be positioned at or adjacent to a distal end of a central branch of the monitoring element. The camera may be capable of capturing hemispherical images of the esophagus (e.g., 120° hemispherical images, 150° hemispherical images, 120° to 150° hemispherical images, up to 180° hemispherical images, 120° to 180° hemispherical images, etc.) or cylindrical images of the esophagus (e.g., a panoramic, or 360°, view, etc.). Thus, some embodiments of the camera may include a hemispherical lens (e.g. a fisheye lens, etc.) or a cylindrical lens (e.g., panoramic lens, etc.).

A system according to this disclosure may also include a light source. A light source may illuminate the esophagus while obtaining images of the inner surface of the esophagus with the camera. The light source may emit one or more wavelengths of visible light, including so-called "white light," and/or one or more wavelengths of electromagnetic radiation (e.g., ultraviolet radiation, infrared radiation, etc.) may be used to reveal trauma or evidence of trauma (e.g., increased blood flow to a particular location, etc.) before it would otherwise be visible when illuminated with white light.

A system for monitoring a condition of a subject's esophagus according to this disclosure may include one or more position sensors. The position sensor(s) may be adapted to be placed at a fixed location relative to a path along which the esophageal monitoring device will be inserted into and removed from the subject's esophagus (e.g., along a length of an insertion component from which the esophageal monitoring device will be deployed, etc.). As a non-limiting example, a position sensor may be capable of placement adjacent to a subject's nares or mouth, past which the esophageal monitoring device will pass as the esophageal monitoring device is inserted into or removed from the subject's esophagus. As the esophageal monitoring device or features thereof (e.g., position reference features detectable by the position sensor(s), etc.) move past the position sensor(s), the position sensor(s) may determine an extent to which (e.g., a distance, etc.) the esophageal monitoring device has been inserted into the subject's esophagus. Thus, each position sensor may also be used to determine a location of a distal end of the esophageal monitoring device within the esophagus, or a distance the distal end of the esophageal monitoring device has been inserted into the esophagus. From such information, the position sensor(s) may also determine a position of the camera from a top of the esophagus.

In embodiments where the system includes one or more position sensors, the esophageal monitoring device may include position reference features. The position reference features may be disposed along a length of a portion of the esophageal monitoring device (e.g., along a proximal element of the esophageal monitoring device, etc.). Alternatively, position reference features may be disposed along the length of an insertion component for the esophageal monitoring device. Adjacent position reference features may be spaced apart from one another at a fixed distance, or interval. In a specific embodiment, adjacent position reference features may be spaced 5 mm apart from one another. In another specific embodiment, adjacent position reference features may be spaced 1 cm apart from each other. The position reference features may be detectable by a position sensor of a known type, which may be placed at a fixed location adjacent to the esophageal monitoring device as the esophageal monitoring device is introduced into or withdrawn from a subject's esophagus.

In another aspect, esophageal monitoring devices are disclosed.

Other aspects, as well as features and advantages of various aspects, of the disclosed subject matter will become apparent to those of ordinary skill in the art through consideration of the ensuing description, the accompanying drawings, and the appended claims.

DETAILED DESCRIPTION

Figures 3, 4:
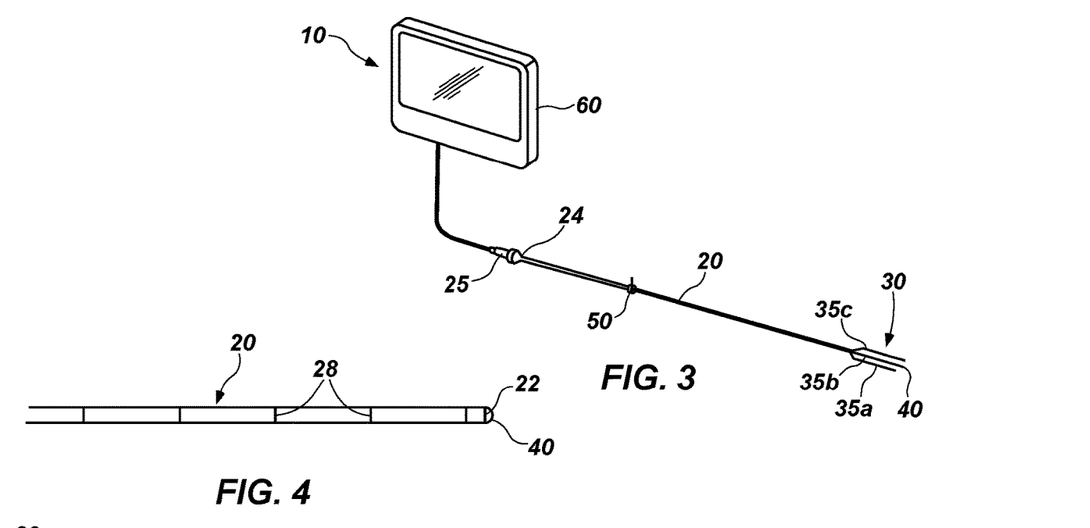
FIG. 4 shows a distal portion of an embodiment of an insertion component of an esophageal monitoring system according to this disclosure, with a distal feature of an embodiment of an esophageal monitoring device protruding from a distal end of the insertion component.

FIGS. 2 and 3 illustrate an embodiment of a system 10 according to this disclosure, which system 10 may also be referred to as an "esophageal monitoring system." The system 10 is capable of monitoring a condition of a subject's esophagus while an ablation procedure is being performed on the posterior wall of the left atrium of the subject's heart (i.e., during a left atrial ablation procedure). As illustrated, the system 10 includes an insertion component 20, an esophageal monitoring device 30, a camera 40, a position sensor 50, and a monitor 60.

In FIG. 2, the esophageal monitoring device 30 is located within a lumen 21 (FIG. 5) of the insertion component 20, but the camera 40, which is located on a distal end 32 (FIG. 6) of the esophageal monitoring device 30, may be located at or just outside of (i.e., distal to) the distal end 22 of the insertion component 20.

In FIG. 3, a monitoring element 34 of the esophageal monitoring device 30 has been deployed from a distal end 22 of the insertion component 20, and branches 35a, 35b, 35c of the monitoring element 34 have expanded.

The monitor 60 of a system 10 according to this disclosure may include a display screen 62, a processing element 64, and one or more connectors 66 (e.g., communication ports, etc.).

Figure 10:
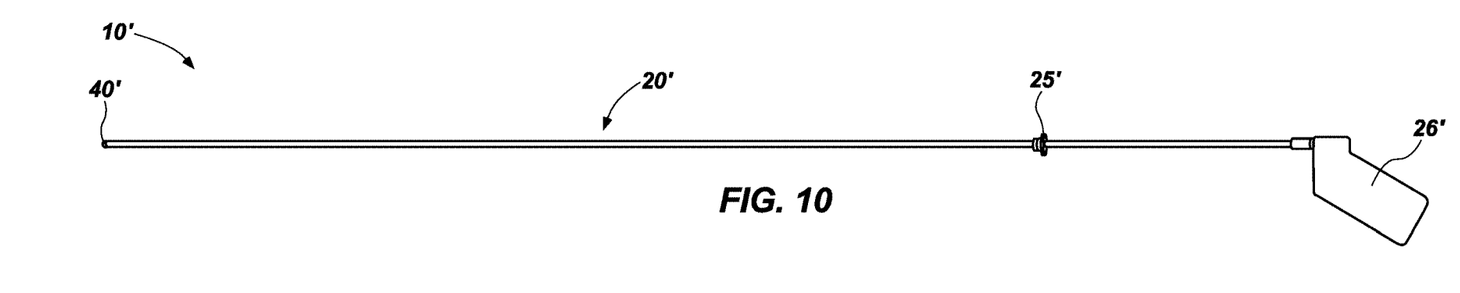
FIG. 10 illustrates another embodiment of an esophageal monitoring system according to this disclosure, including a proximal portion of an esophageal monitoring device and an insertion component over a remainder of the esophageal monitoring device.
Figure 12:
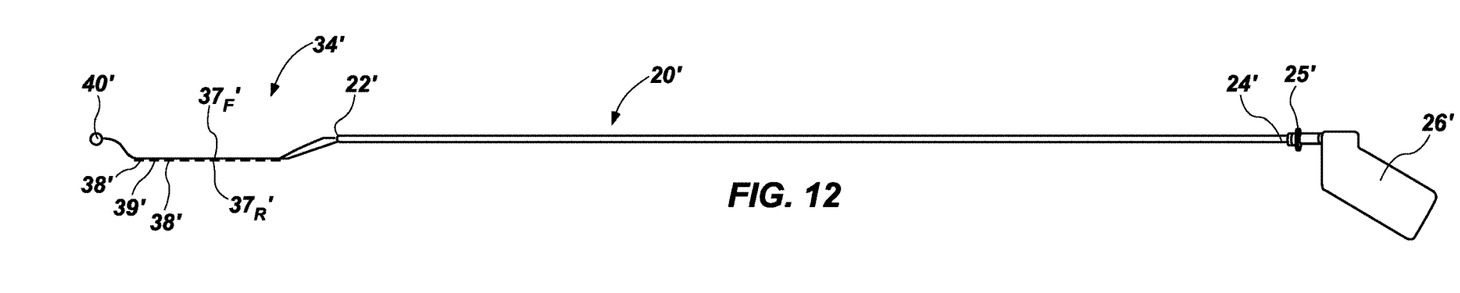
FIG. 12 is a side view of the esophageal monitoring system shown in FIG. 11, with the insertion component pulled proximally over an elongated element of the proximal portion of the esophageal monitoring device, adjacent to or against a handle of the proximal portion, and the monitoring element of the esophageal monitoring device in a deployed orientation.
Figure 13:
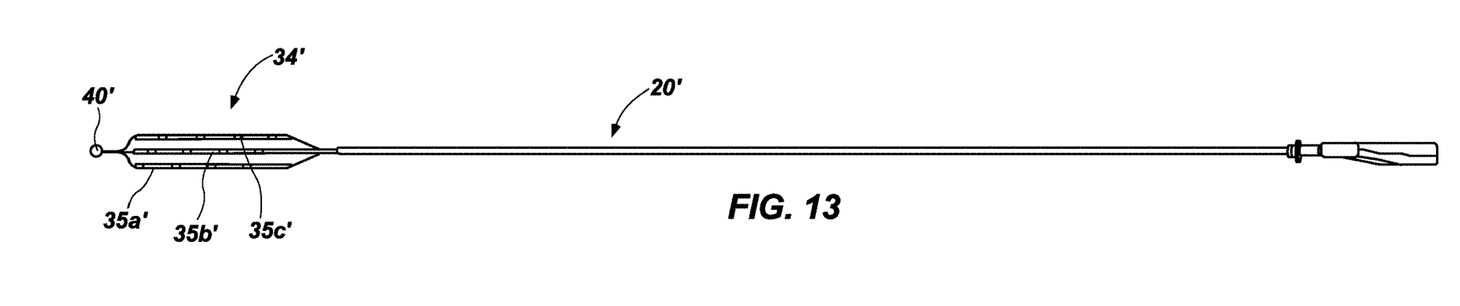
FIG. 13 is a top view of the arrangement shown in FIG. 12.

A connector 66 of the monitor 60 may be configured to couple to, or mate with, a complementary connector of the esophageal monitoring device 30 (e.g., the connector 26' shown in FIGS. 10 and 12, etc.). The connector 66 may comprise any suitable communication port (e.g., a USB (universal serial bus) port, a USB-C port, a proprietary communication port, etc.).

The processing element 64 of the monitor 60 may, under control of one or more programs or applications (or "apps"), communicate with various devices carried by the esophageal monitoring device 30, including the camera 40, and the position sensor 50 (e.g., receive signals and data embodied by the signals from devices carried by the esophageal monitoring device 30 and the position sensor 50, send instructions to devices carried by the esophageal monitoring device 30, etc.). In addition, the processing element 64 may process data conveyed as signals from devices carried by the esophageal monitoring device 30 and output such data to the display screen 62 of the monitor 60. The processing element 64 may comprise a central processing unit (CPU), a graphics processing unit (GPU), a dedicated microcontroller, or the like.

The display screen 62 of the monitor 60 may function under control of the processing element 64 to provide one or more users (e.g., one or more healthcare providers, etc.) with the data in a readily comprehendible form (e.g., as numbers, graphics, etc.). As an example, the display screen 62 may display temperature data in numeric format, as well as in colors to indicate whether or not the displayed temperature values are potentially damaging to a subject's esophagus. As another example, the display screen 62 may display a position of a monitoring element 34 of the esophageal monitoring device 30 within a subject's esophagus. The display screen 62 may, in some embodiments, provide a user of the system 10 with information about the pressure, or force, between the monitoring element 34 of the esophageal monitoring device 30 and the wall of the esophagus against which the monitoring element 34 is positioned, as well as an interpretation of the potential causes, the actual causes, the potential effects, and/or the actual effects of such pressure.

In addition, the monitor (e.g., a touch-sensitive display screen 62, etc.) may enable a user to provide inputs that control operation of the monitor 60 and/or the esophageal monitoring device 30.

The insertion component 20 of the system 10 may be capable of facilitating introduction of the esophageal monitoring device 30 into a subject's esophagus, deploying the monitoring element 34 of the esophageal monitoring device 30, retracting the monitoring element 34 of the esophageal monitoring device 30 (e.g., into the insertion component 20, etc.), and/or removing the esophageal monitoring device 30 from the subject's esophagus. The insertion component 20 may comprise a flexible catheter or another flexible tubular element. That includes a distal end 22 (e.g., the end that is to be introduced into the esophagus first), a proximal end 24 configured to remain outside of the subject's body, and a lumen 21 (FIG. 5) extending between the distal end 22 and the proximal end 24. Dimensions of the lumen 21 (e.g., its inner diameter) enable it to receive the esophageal monitoring device 30, including the monitoring element 34 of the esophageal monitoring device 30 when the monitoring element 34 is in a retracted arrangement.

An actuator 25 may be associated with a proximal end 24 of the insertion component 20 and/or a proximal end of the esophageal monitoring device 30 to enable a user (e.g., a healthcare provider, etc.) to control the relative positions of the insertion component 20 and the esophageal monitoring device 30. In some embodiments, the actuator 25 may enable a user to slide the insertion component 20 along a length of the esophageal monitoring device 30. In other embodiments the actuator 25 may enable a user to slide the esophageal monitoring device 30 through the lumen 21 (FIG. 5) of the insertion component 20. As shown, the actuator 25 may comprise an enlarged feature, or a handle, that may be grasped and moved by the user.

Figure 5:
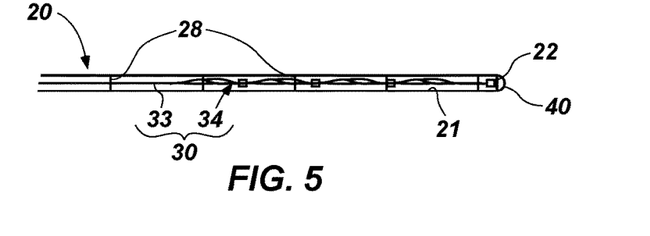
FIG. 5 shows the esophageal monitoring device within a lumen of the insertion component.

FIGS. 4 and 5 illustrate a distal portion of the insertion component 20, with FIG. 4 showing an exterior of the insertion component 20 and the camera 40 protruding from the distal end 22 of the insertion component 20, and FIG. 5 showing features of the esophageal monitoring device 30, including the monitoring element 34 thereof and a portion of a proximal element 33 thereof.

In the illustrated embodiment, position reference features 28 are positioned at fixed intervals along the length of the insertion component 20. The position reference features 28 may be detectable by the position sensor 50 as they pass by (or through) the position sensor 50. The position sensor 50 may send signals to the processing element 64 of the monitor 60, which may then determine a location of the insertion component 20 and/or a distal portion of the esophageal monitoring device 30 (e.g., its distal end 32, the monitoring element 34, etc.) relative to the position sensor 50 and the esophagus (e.g., a distance the insertion component 20 and/or the esophageal monitoring device 30 has/have been inserted into the esophagus, etc.).

Figure 6:
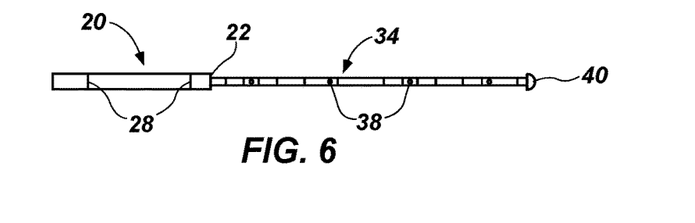
FIG. 6 provides a top view of the distal portion of the embodiment of insertion component shown in FIG. 4, with a monitoring element of the esophageal monitoring device partially deployed from the insertion component.
Figures 7, 8, 9, 18:
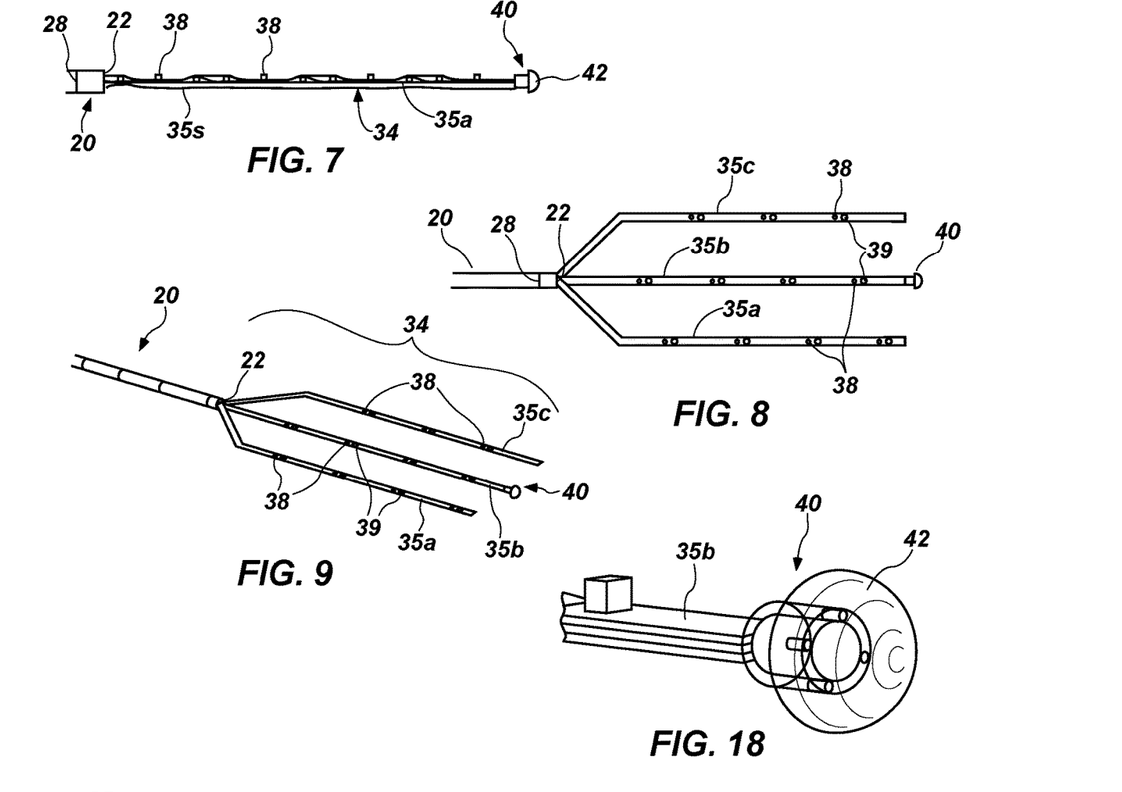
FIG. 7 is a side view illustrating the monitoring element of the esophageal monitoring device fully deployed from the insertion component and occupying a substantially two-dimensional area.
FIG. 8 is a top view of the arrangement illustrated by FIG. 7.
FIG. 9 is a perspective view of the arrangement illustrated by FIG. 7.
FIG. 18 illustrates an embodiment of a camera of an esophageal monitoring device.

FIGS. 6-9 show the monitoring element 34 of the esophageal monitoring device 30 deployed from the distal end 22 of the insertion component 20, with FIG. 6 providing a top view prior to unfolding of branches 35a, 35b, 35c, etc., of the monitoring element 34, FIG. 7 showing a side view of a branch 35a, and FIGS. 8 and 9 showing the branches 35a, 35b, 35c, etc., in a deployed, or an unfolded, arrangement. As illustrated by FIGS. 7 and 9, the deployed monitoring element 34 may be substantially two-dimensional.

The branches 35a, 35b, 35c, etc., of the monitoring element 34 of the esophageal monitoring device 30 may be continuous with the proximal element 33 of the esophageal monitoring device 30. In some embodiments, the proximal element 33 and the monitoring element 34 may comprise a flexible printed circuit board, or "flex PCB" or "flex circuit" that carries conductive traces, or "wires," as well as electrical contacts. The branches 35a, 35b, 35c, etc., of the monitoring element 34 may also include a structural support element 35s (FIG. 7) which may enable the branches 35a, 35b, 35c, etc., to maintain or substantially maintain their relative positions when the monitoring element 34 and its branches 35a, 35b, 35c, etc., are in their deployed arrangement. The structural support element 35s may be carried by (e.g., laminated or otherwise secured to, formed within, etc.) the substrate of each branch 35a, 35b, 35c, etc. (e.g., the flex circuit, etc.). In a specific embodiment, the structural support element 35s may comprise a pre-shaped elongated element formed from a shape memory alloy, such as nitinol (or NiTiNOL—nickel-titanium Naval Ordnance Laboratory), which may assume its intended shape as the structure support element 35s is deployed from the lumen 21 (FIG. 5) of the insertion component 20 and exposed to the temperature within the esophagus (e.g., body temperature, etc.). In a more specific embodiment, the structural support element 35s may comprise a 0.008 inch diameter nitinol wire.

FIGS. 8 and 9 also illustrate an arrangement of sensors 38 and 39 carried by the branches 35a, 35b, 35c of the monitoring element 34 and arranged across an area occupied by the monitoring element 34. Sensors 38 may comprise temperature sensors of a known type (e.g., thermistors, etc.). Sensors 39 may comprise pressure sensors or force sensors of a known type. In some embodiments, the monitoring element 34 may carry sensors 39 that serve as positional markers (e.g., impedance electrodes, etc.), which may be used to anatomically map (e.g., three-dimensionally map, etc.) the location of the monitoring element 34 within the esophagus and relative to the left atrium of the subject's heart (e.g., by impedance-based mapping, etc.) and, when used in conjunction with measurements of the pressure or force exerted on pressure sensors or force sensors of the monitoring element 34, may be used to map the physical relationship between the left atrium and the esophagus, as well as any changes to that physical relationship (e.g., force of the left atrium against the pericardium and the esophagus, etc.).

Turning now to FIGS. 10-16, another embodiment of a system 10' for monitoring a condition of a subject's esophagus during a left atrial ablation procedure is depicted. The system 10' may include all of the components of system 10 (FIGS. 2-9) (i.e., an insertion component 20', an actuator 25' at a proximal end 24 of the insertion component 20', an esophageal monitoring device 30' within a lumen (not shown) of the insertion component 20', a camera 40' at or near a distal end of the esophageal monitoring device 30', an optional light source, a position sensor 50 (FIGS. 2 and 3), and a monitor 60 (FIGS. 2 and 3), with the configuration of the esophageal monitoring device 30' being the primary difference between system 10' and system 10 (FIGS. 2 and 3).

Figures 11, 15:
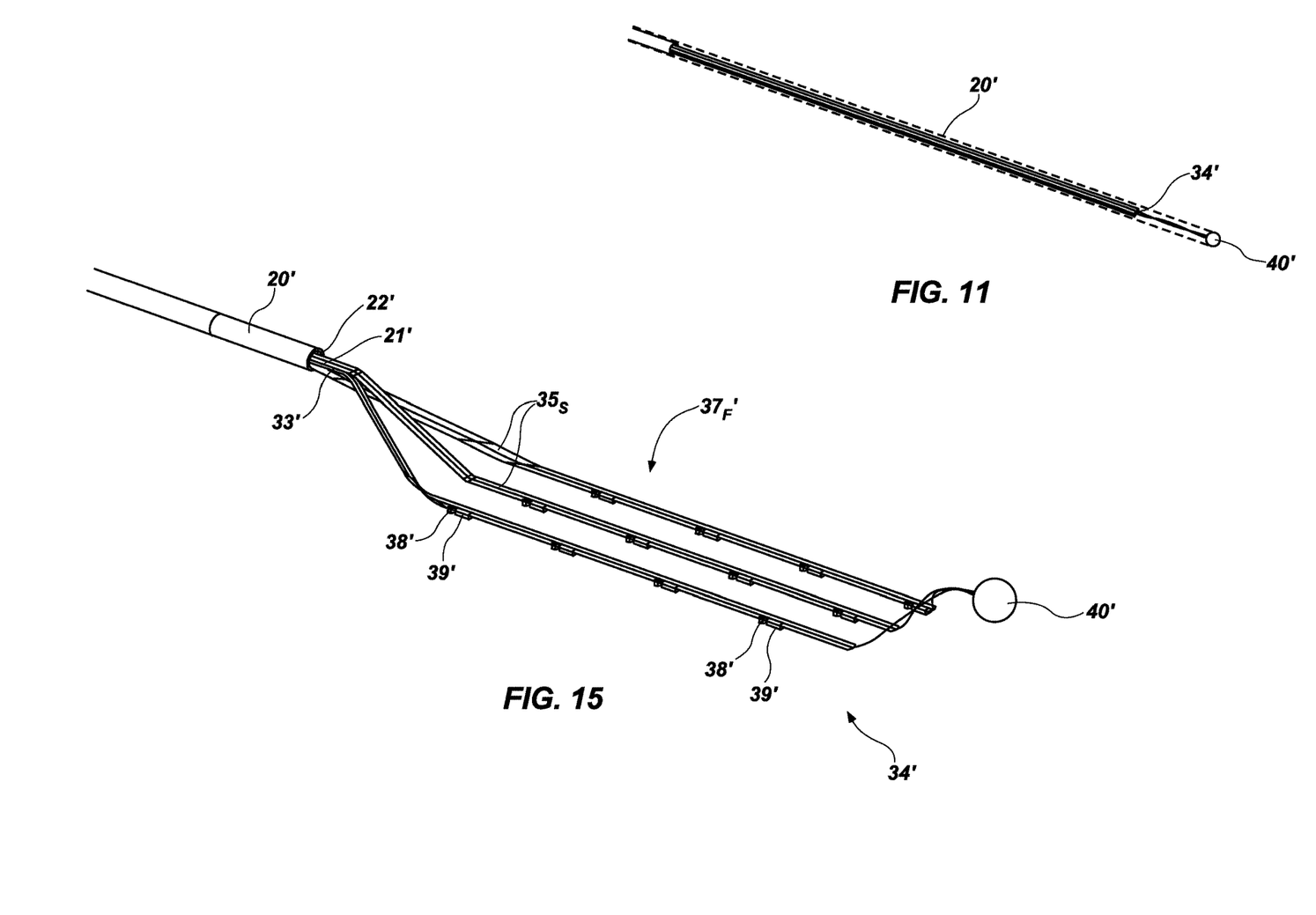
FIG. 11 shows a monitoring element of the esophageal monitoring device within a distal portion of the insertion component.
FIG. 15 is a perspective view of a concave side of the embodiment of monitoring element shown in FIG. 13.
Figures 14, 16:
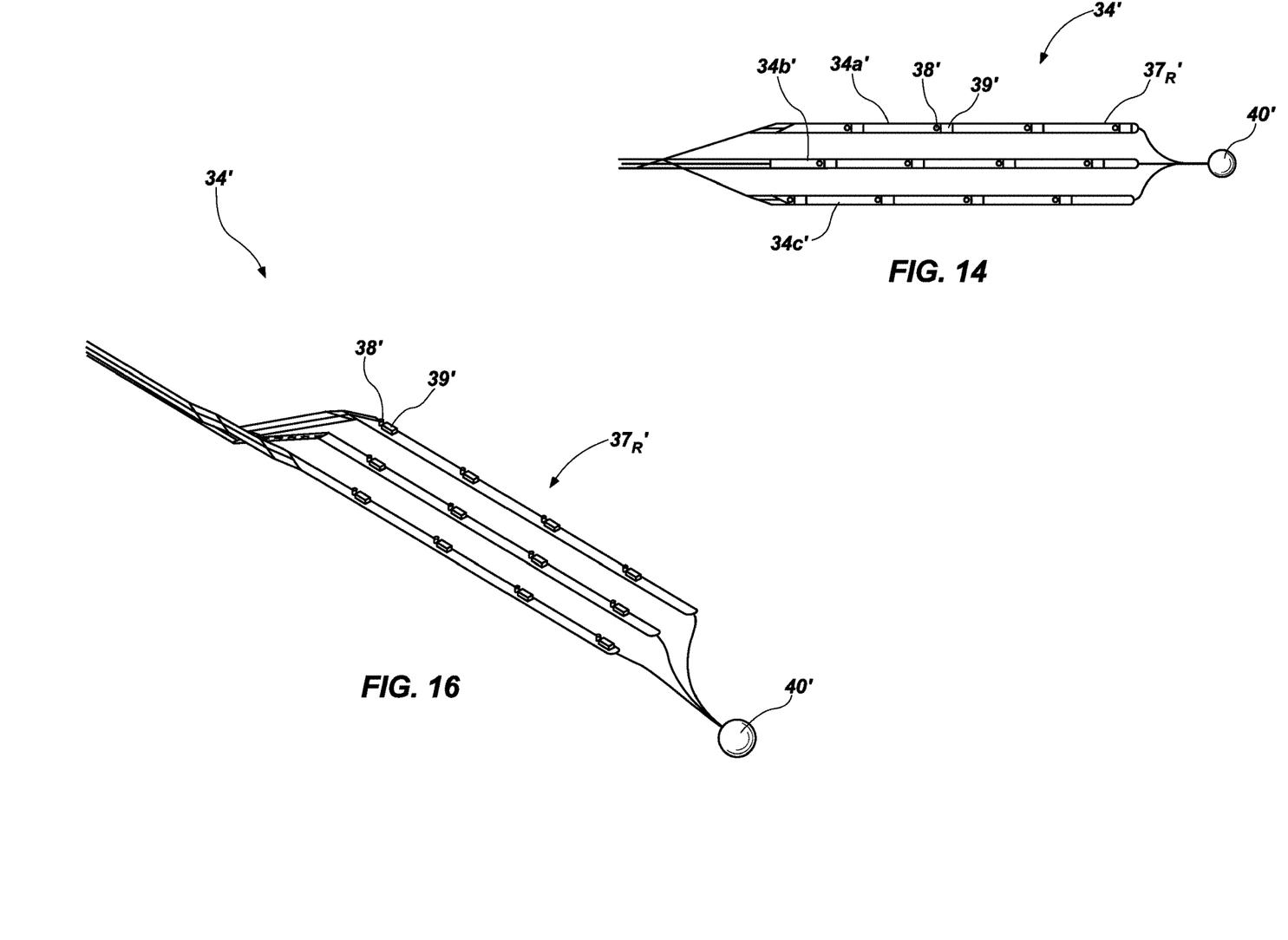
FIG. 14 is an enlarged rear view of the embodiment of monitoring element shown in FIG. 13.
FIG. 16 is a perspective view of a convex side of the embodiment of monitoring element shown in FIG. 13.

In particular, as depicted by FIGS. 12, 15, and 16, the monitoring element 34' of the esophageal monitoring device 30' may occupy a three-dimensional space rather than having a substantially two-dimensional arrangement. More specifically, the branches 35a', 35c', etc., of the monitoring element 34' are bent or curved. As depicted by FIG. 15, a structure support element 35s carried by the substrate (e.g., a flex circuit, etc.) of each branch 35a', 35b', 35c', etc., (e.g., an elongated element formed from a shape memory alloy, such as nitinol, a nitinol wire (e.g., a 0.008 inch diameter nitinol wire, etc.), a thin nitinol band, etc.) may define the shape of each branch 35a', 35b', 35c', etc., (e.g., as it is exposed to an increased temperature (e.g., body temperature, etc.) within the esophagus, etc.) and the relative positions of the branches 35a', 35b', 35c', etc., when they are deployed from the lumen 21 of the insertion component 20'. The branches 35a', 35b', 35c', etc., may be bent or curved and arranged in a manner that facilitates their placement against an interior surface of a subject's esophagus. FIG. 16 illustrates a convex side $37_R'$ of the monitoring element 34, which is configured to be positioned against the interior surface of the esophagus, while FIG. 15 illustrates a concave side $37_F'$ of the monitoring element 34', which is configured to face into a lumen of the esophagus when the monitoring element 34' is positioned against the interior surface of the esophagus. In some embodiments, as the monitoring element 34' is deployed in a subject's esophagus and placed against an interior surface of the esophagus, the branches 35a', 35b', 35c', etc., may flatten out, enabling the monitoring element 34' to be placed against the interior surface of the esophagus without deforming or moving the esophagus.

As shown in FIGS. 14 and 16, sensors 38', 39' may be carried by the concave side of each branch 35a', 35b', 35c', etc., of the monitoring element 34' (i.e., the side that will be placed against an interior surface of the subject's esophagus).

Figure 17:
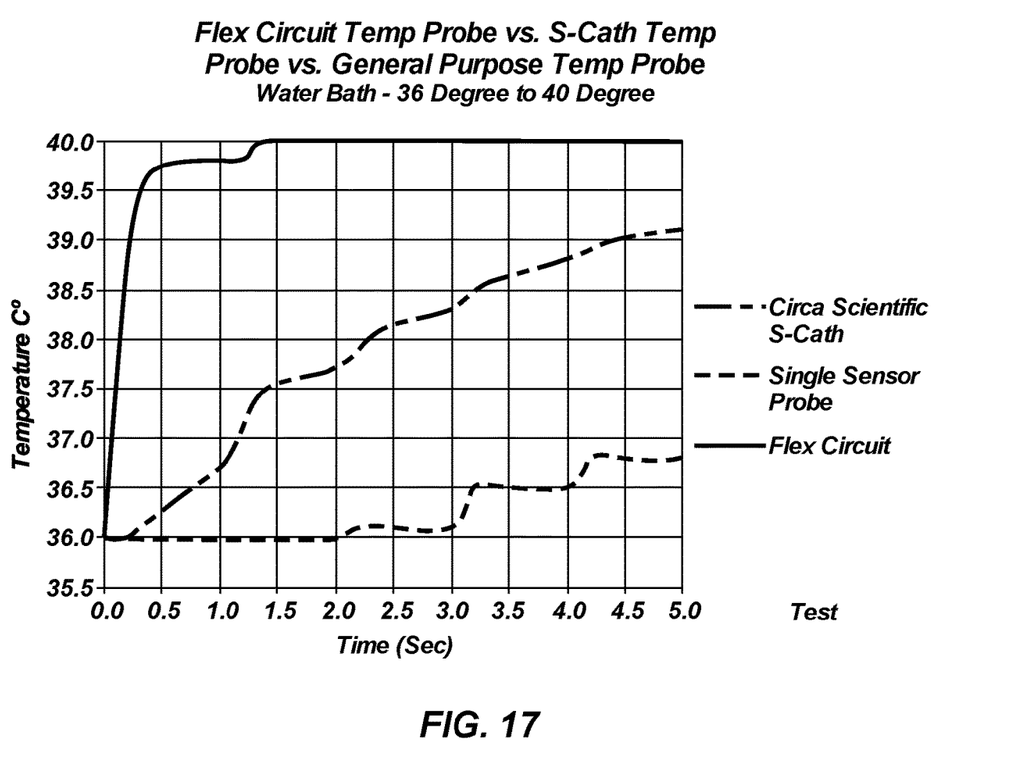
FIG. 17 is a graph showing the time in which temperature sensors of the embodiment of esophageal monitoring device shown in FIGS. 10-16 respond to changes in temperature, and providing a comparison of that time to the times in which temperature sensors of existing devices respond to changes in temperature.

Due to the low thermal mass of flexible printed circuit boards, their use as the substrate for a monitoring element 34', or for each branch 35a', 35b', 35c', etc., of the monitoring element 34', dramatically increases the thermal response time of each temperature sensor (e.g., each sensor 38'). The temperature sensors (e.g., sensors 38') of the monitoring element 34' of the esophageal monitoring device 30' respond to temperature changes within 0.1 second (i.e., one-tenth of a second or less). By way of comparison, the temperature sensors of the CIRCA S-CATH™ esophageal temperature monitor available from CIRCA Scientific, LLC, of Englewood, California, respond to temperature changes in about two (2) seconds while it takes about eight (8) seconds for the temperature sensors of a general purpose esophageal probe to respond to temperature changes. These response times are illustrated by the graph of FIG. 17, in which twelve (12) response times were measured and averaged for temperature sensors of the monitoring element 34' of the esophageal monitoring device 30' (the left-most curve) and compared with average response times for temperature sensors of the CIRCA S-CATH™ esophageal temperature monitor (the center curve), and the Level 1® 9 F general purpose esophageal/rectal temperature probe available from Smiths Medical of Dublin, Ohio (the right-most curve). In those response time analyses, temperature sensors that had been heated to a temperature of 36° C. (e.g., in a warm water bath, etc.) were immersed in a warmer, 40° C. water bath, and the amount of time it took each sensor to respond to a 2° C. rise in temperature (from 36° C. to 38° C.) was measured.

By providing quick response times to changes in temperature, an esophageal monitoring device (e.g., esophageal monitoring device 30', etc.) according to this disclosure may enable a healthcare provider to react more quickly to the exposure of the esophagus to potentially damaging temperatures. Improvement of the healthcare provider's reaction times may decrease the likelihood of damage to the esophagus during a left atrial ablation procedure.

FIG. 18 provides a close-up view of a camera 40, which is located at a distal end 36b of a branch 35b of the monitoring element 34 of the esophageal monitoring device 30 (or at a distal end of a branch 35b' of the monitoring element 34' of the esophageal monitoring device 30'). As illustrated, the camera 40 may include a lens 42 with a dome shape, a hemispherical shape, or any other shape that will enable the camera 40 to capture images around an entirety of the inner surface of the esophagus. A light source (e.g., a source of visible light, a source of infrared radiation, a source of ultraviolet radiation, etc.) may be associated with the camera 40 to enable or enhance visualization of the interior surface of the esophagus.

Figure 19:
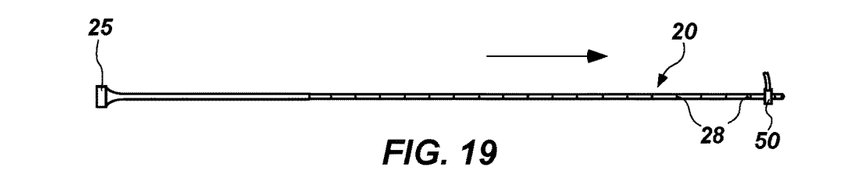
FIGS. 19 and 20 illustrate embodiments of position sensors and position monitoring features of an esophageal monitoring system, which are capable of monitoring the distance the esophageal monitoring device has been inserted into the esophagus and, thus, its position along the esophagus.

With reference to FIG. 19, an embodiment of use of the position sensor 50 and the position reference features 28 on the insertion element 20 is depicted. In particular, FIG. 19 depicts the use of the position sensor 50 and the position reference features 28 while inserting the insertion component 20 and, thus, the esophageal monitoring device 30 (FIGS. 2 and 5-8) into a subject's esophagus. The position sensor 50 may be placed at a fixed location, such as the nares or mouth of the subject. As the insertion component 20 is introduced into the esophagus, it passes by or passes through the position sensor 50. The position sensor 50 may detect each position reference feature 28 on the insertion component 20 that passes thereby or therethrough.

Figure 20:
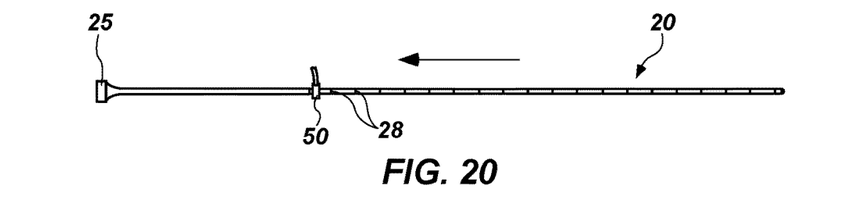

FIG. 20 illustrates use of the position sensor 50 and the position reference features 28 as the insertion component 20 and, thus, the esophageal monitoring device 30 are withdrawn from a subject's esophagus. Again, as each position reference feature 28 on the insertion component 20 passes by or through the position sensor 50, the position sensor 50 detects that position reference feature 28.

In use, the insertion component 20 may initially reside over the monitoring element 34 of the esophageal monitoring device 30, as shown in FIGS. 2, 4, and 5. With the insertion component 20 and the esophageal monitoring device 30 in this arrangement, they may be introduced into a subject's esophagus (e.g., through the subject's nose, through the subject's mouth, etc.). The position of the insertion component 20 and/or the esophageal monitoring device 30 may be monitored (e.g., by the position sensor 50, etc.; see, e.g., FIG. 19) as they are introduced into the esophagus. In addition, the interior surfaces of the esophagus may be visualized (e.g., with the camera 40, etc., with or without illumination) while the insertion component 20 and the esophageal monitoring device 30 are introduced into the esophagus.

Once the distal end 22 of the insertion component 20 has reached a desired location within the esophagus, the monitoring element 34 of the esophageal monitoring device 30 may be deployed from the lumen 21 of the insertion component 20, as depicted by FIGS. 3 and 6-9. In embodiments of the system 10 where the insertion component 20 can be pulled proximally to deploy the monitoring element 34 of the esophageal monitoring device 30, deployment of the monitoring element 34 may occur once the distal end 22 of the insertion component 20 has been advanced to a location beneath a portion of the esophagus located in proximity to the left atrium of the subject's heart. In embodiments where the esophageal monitoring device 30 can be pushed distally out of the distal end 22 of the insertion component 20, deployment of the monitoring element 34 may occur once the distal end 22 of the insertion component 20 has been advanced to a location just above a portion of the esophagus located in proximity to the left atrium of the subject's heart.

Once deployed, the monitoring element 34 may be placed against an interior surface of the esophagus, at a location where the esophagus is located closest to the left atrium of the subject's heart. The monitoring element 34 or, more specifically, sensors carried by the monitoring element 34 (e.g., temperature sensors 38, force sensors 39, etc.) may be used to monitor the surface of the esophagus against which the monitoring element 34 has been placed. Such monitoring may occur during a left atrial ablation procedure and, optionally, before the left atrial ablation procedure (e.g., to provide baseline temperature readings, baseline pressure readings, etc.).

In addition, positional markers (e.g., impedance electrodes, etc.) may be used to three-dimensionally map the location of the monitoring element within the esophagus and relative to the left atrium of the subject's heart. When used in conjunction with measurements of the pressure or force exerted on pressure sensors or force sensors 39 of the monitoring element 34, may be used to map the physical relationship between the left atrium and the esophagus, as well as any changes to that physical relationship (e.g., force of the left atrium against the pericardium and the esophagus, etc.).

Once the left atrial ablation procedure is complete, the monitoring element 34 may be retracted back into the lumen 21 of the insertion component 20, and the insertion component 20 and the esophageal monitoring device 30 may be removed from the subject's esophagus. The position of the insertion component 20 and/or the esophageal monitoring device 30 may be monitored (e.g., by the position sensor 50, etc.; see, e.g., FIG. 20) as they are removed from the esophagus. In addition, the interior surfaces of the esophagus may be visualized (e.g., with the camera 40, etc., with or without illumination) while the insertion component 20 and the esophageal monitoring device 30 are removed from the esophagus.

In embodiments where the interior surfaces of the esophagus have been visualized, a healthcare provider may analyze the interior surfaces to determine whether or not the left atrial ablation procedure has damaged the esophagus. Corrective measures (e.g., surgical treatment, medical treatment, etc.) may then be initiated immediately or within a short period of time (e.g., one day, two days, etc.) of the left atrial ablation procedure.

While the foregoing disclosure relates to esophageal monitoring devices, systems, and methods that are useful during left atrial ablation procedures, the teachings provided herein may also be applicable to devices, systems, and methods for monitoring tissue temperatures during other procedures where adjacent tissues are heated or cooled.

Although the foregoing description contains many specifics, these should not be construed as limiting the scopes of the inventions recited by any of the appended claims, but merely as providing information pertinent to some specific embodiments that may fall within the scopes of the appended claims. Features from different embodiments may be employed in combination. In addition, other embodiments may also lie within the scopes of the appended claims. All additions to, deletions from, and modifications of the disclosed subject matter that fall within the scopes of the claims are to be embraced by the claims.

What is claimed:

1. A method for evaluating a state of an esophagus before, during, and after an ablation procedure conducted on a left atrium of a heart, the method comprising:
visualizing an inner surface of the esophagus while introducing an esophageal monitoring device into the esophagus;
conducting the ablation procedure within the left atrium of the heart;
monitoring a condition of the inner surface of a portion of the esophagus adjacent to the left atrium of the heart while conducting the ablation procedure; and
visualizing the inner surface of the portion of the esophagus adjacent to the left atrium of the heart while withdrawing the esophageal monitoring device from the esophagus.

2. The method of claim 1, wherein:
introducing the esophageal monitoring device into the esophagus comprises:
introducing a temperature probe carrying a plurality of temperature sensors in an area array into the esophagus; and
positioning the temperature probe against the portion of the inner surface of the esophagus adjacent to the left atrium; and
monitoring the condition of the inner surface of the portion of the esophagus adjacent to the left atrium of the heart while conducting the ablation procedure comprises:
monitoring temperatures of the inner surface of the portion of the esophagus adjacent to the left atrium at a plurality of locations adjacent to which the plurality of temperature sensors are positioned.

3. The method of claim 2, wherein introducing the esophageal monitoring device into the esophagus further comprises:
unfolding branches of the temperature probe when the branches of the temperature probe are located adjacent to the portion of the esophagus adjacent to the left atrium.

4. The method of claim 1, wherein:
introducing the esophageal monitoring device into the esophagus comprises:
introducing a pressure probe carrying a plurality of pressure sensors in an area array into the esophagus; and
positioning the pressure probe against the portion of the inner surface of the esophagus adjacent to the left atrium; and
monitoring the condition of the inner surface of the portion of the esophagus adjacent to the left atrium of the heart while conducting the ablation procedure comprises:
monitoring pressure applied to the portion of the inner surface of the esophagus adjacent to the left atrium of the heart by the left atrium at a plurality of locations adjacent to which the plurality of pressure sensors are positioned.

5. The method of claim 4, wherein introducing the esophageal monitoring device into the esophagus further comprises:
unfolding branches of the pressure probe when the branches of the pressure probe are located adjacent to the portion of the esophagus adjacent to the left atrium.

6. The method of claim 1, wherein visualizing the inner surface of the esophagus while introducing the esophageal monitoring device into the esophagus and/or visualizing the inner surface of the portion of the esophagus adjacent to the left atrium of the heart while withdrawing the esophageal monitoring device from the esophagus comprises visualizing the inner surface of the esophagus at fixed distance intervals.

7. The method of claim 6, wherein visualizing the inner surface of the esophagus while introducing the esophageal monitoring device into the esophagus and/or visualizing the inner surface of the portion of the esophagus adjacent to the left atrium of the heart while withdrawing the esophageal monitoring device from the esophagus comprises visualizing the inner surface of the esophagus at intervals of about 5 mm.

8. The method of claim 1, wherein visualizing the inner surface of the esophagus while introducing the esophageal monitoring device into the esophagus and visualizing the inner surface of the portion of the esophagus adjacent to the left atrium of the heart while withdrawing the esophageal monitoring device from the esophagus comprise obtaining a plurality of still images of the inner surface of the esophagus.

9. The method of claim 1, wherein visualizing the inner surface of the esophagus comprises illuminating the inner surface of the esophagus with at least one wavelength of light that will reveal trauma to the inner surface of the esophagus earlier than white light will reveal the trauma.

10. The method of claim 1, further comprising:
comparing a condition of the inner surface of the esophagus while introducing the esophageal monitoring device into the esophagus to a condition of the inner surface of the esophagus while withdrawing the esophageal monitoring device from the esophagus.

11. The method of claim 10, wherein comparing comprises determining an effect of the ablation procedure on the inner surface of the esophagus, including an inner surface of the portion of the esophagus located adjacent to the left atrium of the heart.

12. The method of claim 10, wherein comparing comprises determining an effect of introducing the esophageal monitoring device into the esophagus and/or removing the esophageal monitoring device from the esophagus on the inner surface of the esophagus.

13. The method of claim 10, further comprising:
addressing any damage to the esophagus.

14. A method for evaluating a state of an esophagus during and after a medical procedure, comprising:
conducting the medical procedure;
monitoring a condition of an inner surface of a portion of the esophagus with an esophageal monitoring device while conducting the medical procedure; and
visualizing the inner surface of the portion of the esophagus while withdrawing the esophageal monitoring device from the esophagus.

15. The method of claim 14, further comprising:
visualizing the inner surface of the portion of the esophagus while introducing the esophageal monitoring device into the esophagus.

16. The method of claim 15, further comprising:
comparing a condition of the inner surface while monitoring the condition of the inner surface to a condition of the inner surface while introducing the esophageal monitoring device.

17. The method of claim 16, wherein comparing comprises determining an effect of the medical procedure on the inner surface.

18. The method of claim 15, further comprising:
comparing a condition of the inner surface while withdrawing the esophageal monitoring device to a condition of the inner surface while monitoring the condition of the inner surface and/or to a condition of the inner surface while introducing the esophageal monitoring device.

19. The method of claim 18, wherein comparing comprises determining an effect of the medical procedure on the inner surface.

20. The method of claim 15, further comprising:
determining an effect of introducing the esophageal monitoring device and/or withdrawing the esophageal monitoring device on the inner surface.

* * * * *